(12) United States Patent
Young et al.

(10) Patent No.: US 11,319,231 B2
(45) Date of Patent: May 3, 2022

(54) METHOD FOR MONITORING FLUORESCENT POLYMER ANTISCALANTS IN INDUSTRIAL WATER SYSTEMS

(71) Applicant: Dow Global Technologies LLC, Midland, MI (US)

(72) Inventors: Kaylie L. Young, Sugar Land, TX (US); Clark H. Cummins, Midland, MI (US); William C. Glover, Pearland, TX (US); Robert David Grigg, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 307 days.

(21) Appl. No.: 16/611,909

(22) PCT Filed: Jul. 2, 2018

(86) PCT No.: PCT/US2018/040576
§ 371 (c)(1),
(2) Date: Nov. 8, 2019

(87) PCT Pub. No.: WO2019/027610
PCT Pub. Date: Feb. 7, 2019

(65) Prior Publication Data
US 2021/0078885 A1  Mar. 18, 2021

Related U.S. Application Data

(60) Provisional application No. 62/538,946, filed on Jul. 31, 2017.

(51) Int. Cl.
*C02F 5/12*  (2006.01)
*C07D 235/22*  (2006.01)
(Continued)

(52) U.S. Cl.
CPC .............. *C02F 5/12* (2013.01); *C07D 235/22* (2013.01); *C07D 235/24* (2013.01);
(Continued)

(58) Field of Classification Search
None
See application file for complete search history.

(56) References Cited

U.S. PATENT DOCUMENTS 4,026,815 A * 5/1977 Kallfass .................... C02F 5/14
252/180
4,783,314 A  11/1988 Hoots et al.
(Continued)

OTHER PUBLICATIONS

PCT/US2018/040570, International Search Report and Written Opinion dated Sep. 21, 2018.
(Continued)

*Primary Examiner* — Clare M Perrin
(74) *Attorney, Agent, or Firm* — Amy A. Thekdi

(57) ABSTRACT

The present invention relates to a fluorescently-tagged (co)polymer and use thereof useful as a scale inhibitor in industrial water systems. Said (co)polymer comprises a (i) reactive fluorescent compound selected from a benzodiazole compound (ii) at least one monoethylenically unsaturated acid monomer, and (iii) optionally, at least one monoethylenically unsaturated acid-free monomer.

6 Claims, 3 Drawing Sheets

(51) Int. Cl.
*C07D 235/24* (2006.01)
*C07D 235/26* (2006.01)
*C07D 235/28* (2006.01)
*C07D 271/12* (2006.01)
*C07D 285/14* (2006.01)
*C08F 34/00* (2006.01)
*C08F 134/00* (2006.01)
*C08F 234/00* (2006.01)
*C08F 220/06* (2006.01)
*C08F 220/56* (2006.01)
*C08F 220/58* (2006.01)
*B01D 65/08* (2006.01)
*C02F 1/00* (2006.01)
*C09K 11/06* (2006.01)
*C02F 5/10* (2006.01)

(52) U.S. Cl.
CPC ......... *C07D 235/26* (2013.01); *C07D 235/28* (2013.01); *C07D 271/12* (2013.01); *C07D 285/14* (2013.01); *C08F 34/00* (2013.01); *C08F 134/00* (2013.01); *C08F 220/06* (2013.01); *C08F 220/56* (2013.01); *C08F 220/585* (2020.02); *C08F 234/00* (2013.01); *B01D 65/08* (2013.01); *C02F 1/008* (2013.01); *C02F 5/10* (2013.01); *C02F 2303/22* (2013.01); *C08F 2810/00* (2013.01); *C09K 11/06* (2013.01); *C09K 2211/1483* (2013.01)

(56) References Cited

U.S. PATENT DOCUMENTS

| | | |
|---|---|---|
| 4,992,380 A | 2/1991 | Moriarty et al. |
| 5,043,406 A | 8/1991 | Fong |
| 5,128,419 A | 7/1992 | Fong et al. |
| 5,171,450 A | 12/1992 | Hoots |
| 5,232,603 A * | 8/1993 | Denzinger ............... C02F 5/12 210/698 |
| 5,260,386 A | 11/1993 | Fong et al. |
| 5,378,784 A | 1/1995 | Fong et al. |
| 5,986,030 A * | 11/1999 | Murray ............... C08F 220/60 526/268 |
| 6,251,680 B1 | 6/2001 | Fu et al. |
| 6,312,644 B1 | 11/2001 | Moriarty et al. |
| 6,380,431 B1 | 4/2002 | Whipple et al. |
| 6,645,428 B1 * | 11/2003 | Morris ............... C02F 5/12 252/301.35 |
| 6,838,002 B2 * | 1/2005 | Zeiher ............... B01D 61/22 210/650 |
| 7,148,351 B2 | 12/2006 | Morris et al. |
| 7,601,789 B2 | 10/2009 | Morris et al. |
| 7,875,720 B2 | 1/2011 | Morris et al. |
| 2001/0018503 A1 | 8/2001 | Whipple et al. |
| 2004/0118776 A1 | 6/2004 | Zeiher et al. |
| 2004/0135125 A1 | 7/2004 | Morris et al. |
| 2012/0032093 A1* | 2/2012 | Moore ............... G01N 21/64 250/459.1 |
| 2012/0199783 A1* | 8/2012 | Detering ............... C02F 5/145 252/180 |
| 2014/0183140 A1 | 7/2014 | Atkins et al. |
| 2015/0175460 A1 | 6/2015 | Moore et al. |

OTHER PUBLICATIONS

PCT/US2018/040570, International Preliminary Report on Patentability dated Feb. 4, 2020.
PCT/US2018/040576, International Search Report and Written Opinion dated Sep. 5, 2018.
PCT/US2018/040576, International Preliminary Report on Patentability dated Feb. 4, 2020.

* cited by examiner

METHOD FOR MONITORING FLUORESCENT POLYMER ANTISCALANTS IN INDUSTRIAL WATER SYSTEMS

FIELD OF THE INVENTION

This invention relates generally to the field of reactive fluorescent compounds and (co)polymers made with them. These (co)polymers incorporating reactive fluorescent compounds are useful in industrial water systems.

BACKGROUND OF THE INVENTION

There are many industrial water systems, including, but not limited to, cooling water systems and boiler water systems. Because water resources are becoming limited and efficient utilization of water is required, various methods have been adopted to reduce the amount of water used.

As the methods for reducing the amount of water are put into practice, unfavorable events occur, such as the occurrence of corrosion and the formation of scale, because the quality of the water in the system is progressively deteriorated.

To prevent or minimize these troubles, various kinds of treatment agents for treatment of water systems have been used. It has been found that organic substances, including certain types of treatment polymers, are effective for preventing formation of scale and suppressing the occurrence of corrosion. These certain types of treatment polymers are known to persons of ordinary skill in the art of industrial water treatment and are widely used by themselves or as one of many possible components in scale and corrosion inhibition products. Such treatment polymers generally exhibit activity against scale and corrosion when added to water in an amount in the range of from about 1 to about 100 milligrams of solid component active per liter of water.

When a treatment polymer is used for preventing formation of scale and suppressing the occurrence of corrosion, the concentration of the treatment polymer in the water system is the important factor to perform the desired function with good efficiency. For example, a treatment polymer added to a cooling water system can be consumed by many causes. With consumption, the amount of the treatment polymer dissolved in the cooling water does not remain the same as the amount added to the cooling water. Therefore, it is important for the optimum operation of an industrial water system that practical methods are known to determine the concentration of treatment polymers in the water of the industrial water system.

In general practice, the amount of the treatment polymer added to the water in an industrial water system can be measured using various analytical methods. The use of an inert fluorescent tracer or mass balance measurement method as described in U.S. Pat. Nos. 4,783,314; 4,992,380; and 5,171,450, hereby incorporated by reference, to perform this analysis, is known in the art.

In the inert fluorescent tracer method, an inert fluorescent tracer is added to an industrial water system, with the amount of inert fluorescent tracer added being proportional to the amount of the treatment polymer added. By using a fluorometer to measure the fluorescent signal of the inert fluorescent tracer, the amount of the inert fluorescent tracer can be determined by using a calibration curve to relate the amount of fluorescent signal detected to the amount of the inert fluorescent tracer present. Because the inert fluorescent tracer and the treatment polymer are added to the industrial water system in known proportions, by knowing the amount of inert fluorescent tracer present it also means that the amount of treatment polymer present is known.

The inert fluorescent tracer method can be conducted on-line in real time so that any changes in the amount of treatment polymer being added to the system can be made immediately.

As a complement to the use of an inert tracer system, it has been found that treatment polymers to be used as components of scale and corrosion inhibitors in industrial water systems could be monitored if tagged with a reactive fluorescent compound. The amount of reactive fluorescent compound incorporated into the polymer must be enough so that the fluorescence of the polymer can now be adequately measured, however, it must not be so much that the performance of the polymer as a treatment agent for the water is decreased. Because the concentration of the tagged treatment polymer itself can be determined using a fluorometer, it is now possible to measure consumption of the treatment polymer directly. It is important to be able to measure consumption directly because consumption of a treatment polymer usually indicates that a non-desired event, such as scaling, is occurring. Thus by being able to measure consumption of the polymeric additive, there can be achieved an on-line, real time in situ measurement of scaling activity in the cooling system.

Certain tagged polymers are known, see U.S. Pat. Nos. 5,986,030 and 6,312,644, hereby incorporated by reference. However, there is not an abundance of viable tagged polymers for use in industrial water systems. Therefore, it is desirable to provide additional tagged polymers that have a fluorescent signal so that you can use a fluorometer to measure the fluorescent signal of the tagged treatment polymer and determine the concentration of tagged treatment polymer currently present in the industrial water system from that information.

It is known that tagging of polymers is difficult to accomplish because of the difficulty in chemically combining fluorescent moieties with non-fluorescent polymers. In order to synthesize tagged treatment polymers it is also desirable to provide reactive fluorescent compounds that are readily polymerized to form tagged treatment polymers.

BRIEF SUMMARY OF THE INVENTION

A first embodiment of the present invention is a method for maintaining the desired amount of a benzodiazole-tagged (co)polymer in an industrial water system comprising the steps of: a) adding a benzodiazole-tagged (co)polymer to water such that a desired concentration of said benzodiazole-tagged (co)polymer is present in said water, wherein the benzodiazole-tagged (co)polymer comprises: (i) a benzodiazole compound, or salt thereof, represented by one or more of the following formulas:

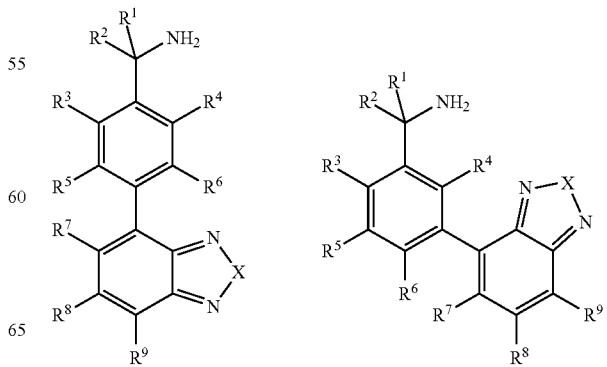

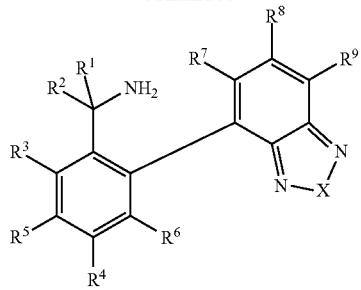

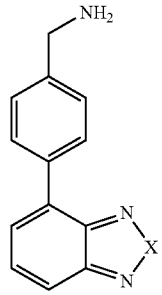

wherein X is oxygen or sulfur. Preferably the benzothiadiazole containing compound is (4-(benzo[c][1,2,5]thiadiazol-7-yl)phenyl)methanamine and salts thereof, preferably hydrochloride salt.

In one embodiment of the invention disclosed herein above, the fluorescently-tagged (co)polymer comprises: (ii) at least one monoethylenically unsaturated acid monomer, preferably acrylic acid, methacrylic acid, crotonic acid, vinylacetic acid, maleic acid, maleic anhydride, 1,2,3,6-tetrahydrophthalic anhydride, 3,6-epoxy-1,2,3,6-tetrahydrophthalic anhydride, 5-norbornene-2,3-di-carboxylic anhydride, bicyclo-[2.2.2]-5-octene-2,3-dicarboxylic anhydride, 3-methyl-1,2,6-tetrahydrophthalic anhydride, 2-methyl-1,3,6-tetrahydrophthalic anhydride, itaconic acid, mesaconic acid, fumaric acid, citraconic acid, 2-acrylamido-2-methylpropanesulfonic acid, allylsulfonic acid, allylphosphonic acid, allyloxybenzenesulfonic acid, 2-hydroxy-3-(2-propenyloxy)-propanesulfonic acid, isopropenylphosphonic acid, isopro-penylsulfonic acid, vinylphosphonic acid, styrenesulfonic acid, vinylsulfonic acid, or the alkali metal or ammonium salts thereof and (iii) optionally, one or more at least one monoethylenically unsaturated acid-free monomer, preferably methyl acrylate, ethyl acrylate, butyl acrylate, methyl methacrylate, ethyl methacrylate, butyl methacrylate and isobutyl methacrylate; hydroxyalkyl esters of acrylic or methacrylic acids such as hydroxyethyl acrylate, hydroxypropyl acrylate, hydroxyethyl methacrylate, hydroxypropyl methacrylate, acrylamide, methacrylamide, N-t-butylacrylamide, N-methylacrylamide, N,N-dimethyl-acrylamide, acrylonitrile, methacrylonitrile, allyl alcohol, phosphoethyl methacrylate, 2-vinylpyridene, 4-vinylpyridene, N-vinylpyrrolidone, N-vinylformamide, N-vinylimidazole, vinyl acetate, or styrene.

DETAILED DESCRIPTION OF THE INVENTION

Figure 1:
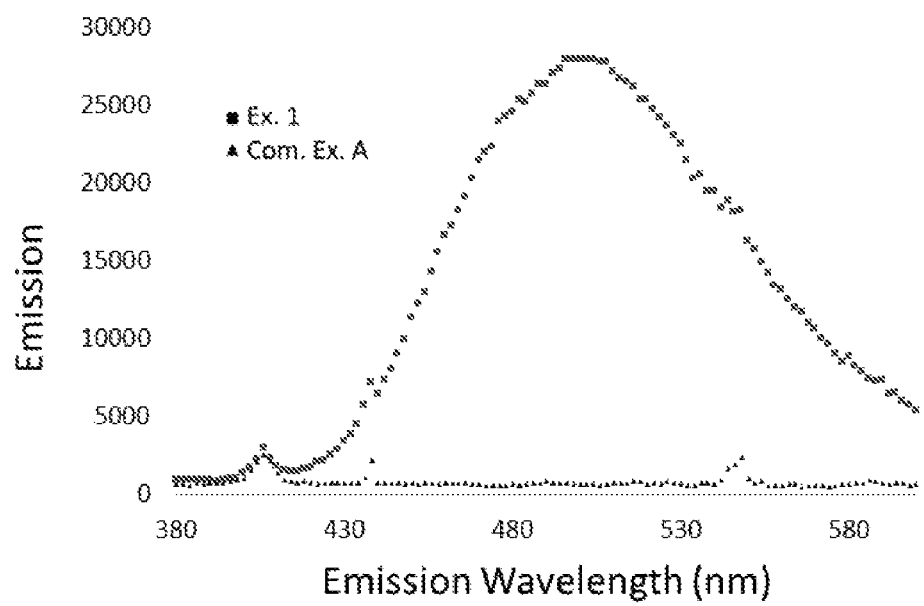
FIG. 1 is a plot of the photoluminescence of Example 1 and Comparative Example A.

The scale inhibitor composition according to the present invention comprises an aqueous solution of a fluorescently-tagged (co)polymer and method of use with said tagged

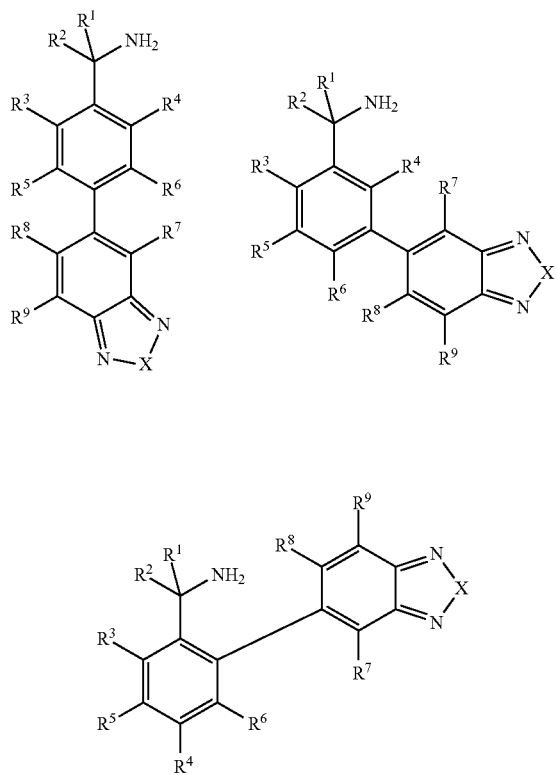

wherein $R^1$ to $R^9$ are independently H, a $C_1$ to $C_{12}$ alkyl group, a $C_1$ to $C_{12}$ aryl group, $-SO_3^-$, $-PO_3^{2-}$, $-CO_2$, or $-N^+R^{10}{}_3$ wherein each $R^{10}$ is independently H or $C_1$ to $C_{12}$ alkyl and X is oxygen or sulfur, b) using a fluorometer to detect a fluorescent signal of said benzodiazole-tagged polymer; c) converting the fluorescent signal of the polymer to a concentration of said benzodiazole-tagged polymer; and d) adjusting the concentration of said benzodiazole-tagged copolymer according to what the desired concentration is for said benzodiazole-tagged copolymer in the industrial water system.

Another embodiment of the present invention is a method to inhibit scale in an industrial water system comprising the steps of: a) providing a scale inhibitor to an industrial water system susceptible to unwanted scaling and b) adding to the water of said industrial water system from 0.1 ppm to 100 ppm of a scale inhibitor, wherein said scale inhibitor is a benzodiazole-tagged copolymer as disclosed herein above.

Preferably the benzodiazole compound, or salt thereof, is represented by the following formula:

(co)polymers to provide a means for achieving better monitoring in industrial water systems.

The reactive fluorescent compound of the present invention is a benzodiazole containing compound, or salt thereof, represented by one or more of the following formulas:

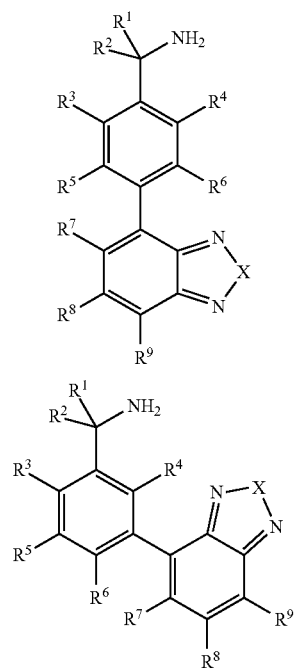

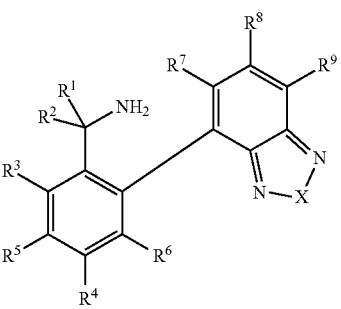

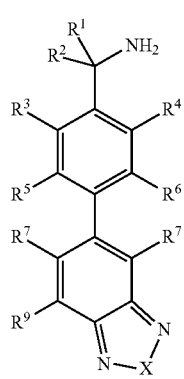

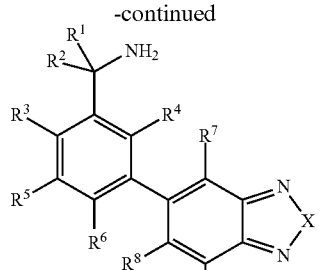

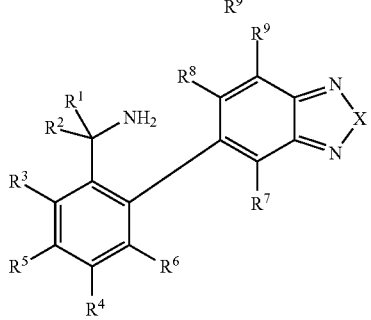

wherein $R^1$ to $R^9$ are independently H, a $C_1$ to $C_{12}$ alkyl group, a $C_1$ to $C_{12}$ aryl group, $-SO_3^-$, $-PO_3^{2-}$, $-CO_2$, or $-N^+R^{10}_3$, wherein each $R^{10}$ is independently H or $C_1$ to $C_{12}$ alkyl and X is oxygen or sulfur.

In one embodiment of the present invention, the reactive fluorescent compound is a benzodiazole containing compound having the following formula:

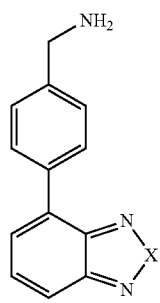

wherein X is oxygen or sulfur. Preferably, the benzothiadiazole containing compound is (4-(benzo[c][1,2,5]thiadiazol-7-yl)phenyl)methanamine and salts thereof, preferably hydrochloride salt.

The fluorescent benzodiazole compound can be reacted with a homopolymer or copolymer to provide a fluorescent-tagged (co)polymer comprising said benzodiazole compounds. As used herein after, the term "(co)polymer means a homopolymer and/or a (co)polymer. Further, "copolymer" or "copolymerization" means a copolymer having two or more comonomers, for example, two, three, four, five, or more comonomers.

Preferably, at least one of the (co)monomers include monoethylenically unsaturated acid. Suitable monoethylenically unsaturated acids include, for example, mono-acids, di-acids or polyacids and the acids may be carboxylic acids, sulphonic acids, phosphonic acids, salts or combinations thereof. If used, the monoethylenically unsaturated acids are preferably selected from one or more of acrylic acid, methacrylic acid, crotonic acid, vinylacetic acid, maleic acid, maleic anhydride, 1,2,3,6-tetrahydrophthalic anhydride, 3,6-epoxy-1,2,3,6-tetrahydrophthalic anhydride, 5-norbornene-2,3-di-carboxylic anhydride, bicyclo-[2.2.2]-5-octene-2,3-dicarboxylic anhydride, 3-methyl-1,2,6-tetrahydrophthalic anhydride, 2-methyl-1,3,6-tetrahydrophthalic anhydride, itaconic acid, mesaconic acid, fumaric acid, citraconic acid, 2-acrylamido-2-methylpropanesulfonic acid, allylsulfonic acid, allylphosphonic acid, allyloxybenzenesulfonic acid, 2-hydroxy-3-(2-propenyloxy)-propanesulfonic acid, isopropenylphosphonic acid, isopro-penylsulfonic acid, vinylphosphonic acid, styrenesulfonic acid, vinylsulfonic acid and the alkali metal or ammonium salts thereof. Most preferably, the one or more monoethylenically unsaturated acids are acrylic acid, methacrylic acid, maleic acid and the alkali metal salts thereof. The monoethylenically unsaturated acids preferably represent at least 60 percent by weight of the total (co)monomers weight, most preferably at least 100 percent by weight of the total (co)monomers weight.

In addition, the (co)polymers may contain, as polymerized units, one or more monoethylenically unsaturated acid-free monomers. Suitable monoethylenically unsaturated acid-free monomers include ($C_1$ to $C_4$) alkyl esters of acrylic or methacrylic acids such as methyl acrylate, ethyl acrylate, butyl acrylate, methyl methacrylate, ethyl methacrylate, butyl methacrylate and isobutyl methacrylate; hydroxyalkyl esters of acrylic or methacrylic acids such as hydroxyethyl acrylate, hydroxypropyl acrylate, hydroxyethyl methacrylate, and hydroxypropyl methacrylate. Other monoethylenically unsaturated acid-free monomers are acrylamides and alkyl-substituted acrylamides including acrylamide, methacrylamide, N-t-butylacrylamide, N-methylacrylamide, and N,N-dimethyl-acrylamide. Other examples of monoethylenically unsaturated acid-free monomers include acrylonitrile, methacrylonitrile, allyl alcohol, phosphoethyl methacrylate, 2-vinylpyridene, 4-vinylpyridene, N-vinylpyrrolidone, N-vinylformamide, N-vinylimidazole, vinyl acetate, and styrene. If used, the monoethylenically unsaturated acid-free monomers are preferably selected from one or more of ethyl acrylate, butyl acrylate, methyl methacrylate, butyl methacrylate, isobutyl methacrylate, hydroxyethyl acrylate, hydroxypropyl acrylate, hydroxyethyl methacrylate, acrylamide, methacrylamide, N-t-butylacrylamide, phosphoethyl methacrylate, vinyl acetate, and styrene. If used, each one or more monoethylenically unsaturated acid-free monomers preferably represent greater than 1 percent by weight of the total (co)monomers weight, preferably less than 60 percent by weight of the total (co)monomers weight.

If desired, it is possible to incorporate polyethylenically unsaturated compounds into the polymerization. Polyethylenically unsaturated compounds function as crosslinking agents and will result in the formation of higher molecular weight (co)polymers.

In one embodiment, the (co)polymers contain at least one amine-sulfide terminal moiety resulting from the attachment of the sulfur group of the amine-thiol to the (co)polymer chain. Most preferably, the (co)polymers contain an amine-sulfide terminal moiety or oxidized sulfide (e.g., sulfoxide, sulfone) as the only pendant amine moiety in the (co)polymer. It is also preferred that the (co)polymers are amine-sulfide terminated (co)polymers of acrylic acid or methacrylic acid and salts thereof. More preferably, the (co)polymers of the present invention are amine-sulfide terminated (co)polymers of acrylic acid or methacrylic acid or salts thereof with each other, maleic acid, maleic anhydride, 1,2,3,6-tetrahydrophthalic anhydride, 3,6-epoxy-1,2, 3,6-tetrahydrophthalic anhydride, 5-norbornene-2,3-dicarboxylic anhydride, itaconic acid, fumaric acid, acrylamide, methacrylamide, N-t-butylacrylamide, N-methylacrylamide, N,N-di-methylacrylamide, 2-acrylamido-2-methylpropanesulfonic acid, methyl acrylate, ethyl acrylate, butyl acrylate, methyl methacrylate, butyl methacrylate, isobutyl methacrylate, hydroxyethyl acrylate, hydroxypropyl acrylate, hydroxyethyl methacrylate and salts thereof.

The (co)polymers of the present invention are prepared by a polymerization process which can be conducted as a cofeed, heel, semi-continuous or continuous process. Preferably, the polymerization is conducted as a cofeed process wherein substantially all of the one or more monomers, the initiator and the amine-thiol chain transfer agent are metered ("fed") into a polymerization reactor. Preferably, the one or more monoethylenically unsaturated monomers, the amine-thiol chain transfer agent and the initiators are introduced into the reaction mixture as separate streams which are fed linearly (i.e., at constant rates). If desired, the streams can be staggered so that one or more of the streams are completed before the others. Generally, the feeds are conducted for from 5 minutes to 5 hours, preferably from 30 minutes to 4 hours, and most preferably from 1 hour to 3 hours.

When the process of the present invention is run as a heel process, a portion of the one or more monoethylenically unsaturated monomers, the one or more amine-thiol chain transfer agents, and/or a portion of the initiators are initially added to the reactor. The remainder of any of these reactants are then fed into the reactor in the same manner as described above for the cofeed process.

The processes by which the (co)polymers of the present invention are prepared are preferably aqueous processes, substantially free of organic solvents. The water may be introduced into the reaction mixture initially, as a separate feed, as the solvent for one or more of the other components of the reaction mixture or some combination thereof. Generally, the polymerizations have a final solids levels in the range of from 20 percent to 80 percent by weight of the reaction mixture, preferably in the range of from 30 to 70 percent by weight, and most preferably from 40 to 70 percent by weight of the reaction mixture.

The polymerization reaction may be conducted at an elevated temperature and will depend on the choice of initiator, and target molecular weight. Generally, the temperature of the polymerization is up to the boiling point of the mixture although the polymerization can be conducted under pressure if higher temperatures are used. The reaction can be conducted under any suitable atmosphere such as for example, air, nitrogen or inert gas. Preferably, the temperature of the polymerization is from 25° C. to 110° C. and most preferably from 40° C. to 105° C.

Suitable initiators for preparing the (co)polymers are any conventional water-soluble initiators. One class of suitable initiators are free-radical initiators such as hydrogen peroxide, certain alkyl hydroperoxides, dialkyl peroxides, persulfates, peresters, percarbonates, ketone peroxides and azo initiators. Specific examples of suitable free-radical initiators include hydrogen peroxide, t-butyl hydroperoxide, di-t-butyl peroxide, ammonium persulfate, potassium persulfate, sodium persulfate, t-amyl hydroperoxide, methylethyl ketone peroxide, 2,2'-azobis(2-amidinopropane), 2,2'-azobis (N,N'-dimethyleneisobutyramidine) dihydrochloride, 2,2'-azobis(2-amidinopropane) dihydrochloride, and 4,4'-azo-bis (4-cyanopentanoic acid). The free-radical initiators are typically used in amounts of from 1 percent to 50 percent based on the total (co)monomers weight.

Water-soluble redox initiators may also be used. These initiators include, but are not limited to, sodium bisulfite, sodium sulfite, hypophosphites, hydroxyl amine sulfate, isoascorbic acid, sodium formaldehyde-sulfoxylate and the like, used with suitable oxidizing agents, such as the thermal initiators noted above. The redox initiators are typically used in amounts of from 0.05 percent to 10 percent, based on the weight of total (co)monomers.

The pH of the polymerizing (co)monomer mixture is preferably highly acidic, especially when using cysteine or aminoethane thiol as the chain transfer agent. For example, when cysteine is used as the chain transfer agent, the preferred pH is below 4 and most preferably below 2. Other amine-thiol chain transfer agents are less sensitive to pH and are preferably used at a pH below 6. The pH of the polymerizing monomer mixture can be controlled by a buffer system or by the addition of a suitable acid or base. The preferred pH of the polymerizing monomer mixture may also be selected to suit the choice of any redox couple used as an initiator.

The polymerizing (co)monomer mixture is preferably substantially free of any metal ions. The addition of metal ions to the polymerizing monomer mixture adds to the cost of the process, may necessitate a separation or purification step, may discolor the product, and introduces contaminants.

The process of preparing the (co)polymers generally results in good conversion of the monomers into polymer product. However, if residual monomer levels in the polymer mixture are undesirably high for a particular application, their levels can be reduced by any of several techniques.

One common method for reducing the level of residual monomer in a (co)polymer mixture is post-polymerization addition of one or more initiators or reducing agents which can assist scavenging of unreacted monomer.

Preferably, any post-polymerization additions of initiators or reducing agents are conducted at or below the polymerization temperature. The initiators and reducing agents suitable for reducing the residual monomer content of (co) polymer mixtures are well known to those skilled in the art. Generally, any of the initiators suitable for the polymerization are also suitable for reducing the residual monomer content of the (co)polymer mixture.

The level of initiators or reducing agents added as a means for reducing the residual monomer content of the (co) polymer mixture should be as low as possible to minimize contamination of the product. Generally, the level of initiator or reducing agent added to reduce the residual monomer content of the (co)polymer mixture is in the range of from 0.1 to 2, and preferably from 0.5 to 1 mole percent based on the total amount of polymerizable (co)monomers.

The (co)polymers are preferably water-soluble. The water-solubility is affected by the molecular weight of the (co)polymers and the relative amounts, and the hydrophilicity, of the monomer components incorporated into the (co)polymer. Generally, the weight average molecular weights (Mw) of the (co)polymers are up to 50,000 preferably from 500 to 25,000 and most preferably from 1,000 to 15,000.

In one embodiment of the present invention, the fluorescently-tagged (co)polymer is made by the well-known process of (trans)amidation derivatization of a pre-existing (co)polymer by the reaction of a pendent carbonyl group on the (co)polymer with a fluorescent benzodiazole compound of the present invention. When attached, said fluorescently-tagged (co)polymer is detectable by fluorimetric techniques.

The (trans)amidation reaction is conducted in an aqueous reaction mixture generally, employing a (co)polymer that is water soluble at the concentration used, or is introduced as held within a latex, and in addition, employing benzodiazole compound of the present invention that is water soluble. The reaction mixture preferably is fluid. The product (co)polymer resulting from the (trans)amidation derivatization reaction may possibly have its solubility characteristics so altered by the incorporation of the fluorescent group that it precipitates, or partially precipitates, from the reaction mixture.

In another embodiment of the present invention, the fluorescent benzodiazole compound may be polymerized into the fluorescently-tagged (co)polymer.

The amount of fluorescent benzodiazole compound that is used should be an amount sufficient to allow the (co)polymer to be detected in the aqueous environment that it is used. The minimum amount of fluorescent moiety that can be used is that amount which gives a signal-to-noise ratio (S/N) of 3 at the desired (co)polymer dosage. The signal-to-noise ratio is that value where the magnitude of the transduced signal (including but not limited to electronic and optical signals) due to the presence of a target analyte in a measurement device is greater than or equal to a level three (3) times the magnitude of a transduced signal where the analyte (species) of interest is not present in the measurement device.

The amount of reactive fluorescent compound in the fluorescently-tagged (co)polymer is in the range of from 0.01 weight percent to 10.0 weight percent, preferably from 0.1 weight percent to 5 weight percent, and most preferably from 1 weight percent to 3 weight percent based on the total weight of the fluorescently-tagged (co)polymer.

Once created, the fluorescent-tagged (co)polymers of the present invention can be used as scale inhibitors in any industrial water system where a scale inhibitor is needed. Industrial water systems, include, but are not limited to, reverse osmosis systems, cooling tower water systems (including open recirculating, closed and once-through systems); petroleum wells, downhole formations, geothermal wells and other oil field applications; boilers and boiler water systems; thermal desalination systems, mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

As stated previously, these fluorescent-tagged (co)polymers function as scale inhibitors. As these (co)polymers are consumed performing that function, their fluorescent signal will decrease and thus the decrease in the fluorescent signal can be used to indicate that undesired scaling is taking place. The (co)polymer tagged with the reactive fluorescent compound may be used in the industrial water systems singly or in combination with other polymers, which are not tagged.

The amount of the (co)polymer tagged with the reactive fluorescent compound added to an industrial water system is in the range of 0.1 milligrams (mg) to 100 milligrams of the total solid polymer actives per liter of water in the system. This is equivalent to 0.1 part per million (hereinafter "ppm") to 100 ppm.

When used in an industrial water system, the fluorescent signal of the benzodiazole-tagged (co)polymers can be used to determine how much (co)polymer is present in the industrial water system. In one embodiment, a method to do this is described as follows:

A method for maintaining the desired amount of benzodiazole-tagged (co)polymer in an industrial water system comprising the steps of:
a) adding a benzodiazole-tagged (co)polymer to water such that a desired concentration of said benzodiazole-tagged (co)polymer is present in said water; b) using a fluorometer to detect the fluorescent signal of said benzodiazole-tagged polymer, for example an online system or a hand held system;
c) converting the fluorescent signal of the polymer to the concentration of said benzodiazole-tagged polymer; and
d) adjusting the concentration of said benzodiazole-tagged (co)polymer according to what the desired concentration is for said benzodiazole-tagged (co)polymer in the industrial water system.

In another embodiment, a method for maintaining the desired amount of benzodiazole-tagged (co)polymer in an industrial water system is as follows:

A method for maintaining the desired amount of benzodiazole-tagged (co)polymer in an industrial water system comprising the steps of:
a) adding an inert tracer and a benzodiazole-tagged (co)polymer to water such that a desired concentration of said benzodiazole-tagged (co)polymer is present in said water;
b) using a fluorometer to detect the fluorescent signals of the inert tracer and the benzodiazole-tagged (co)polymer, for example an online system or a hand held system;
c) converting the fluorescent signals of the inert tracer and the benzodiazole-tagged (co)polymer to the concentration of the inert tracer and the benzodiazole-tagged (co)polymer; and
d) adjusting the concentration of said benzodiazole-tagged (co)polymer according to what the desired concentration is for said benzodiazole-tagged (co)polymer in the industrial water system.

In another embodiment, a method for use of a benzodiazole-tagged (co)polymer as a scale inhibitor in an industrial water system is as follows:

A method for use of a benzodiazole-tagged (co)polymer as a scale inhibitor in an industrial water system comprising the steps of:
a) adding a benzodiazole-tagged (co)polymer to water such that a desired concentration of said benzodiazole-tagged (co)polymer is present in said water, and
b) adding to the water of said industrial water system from 0.1 ppm to 50 ppm of a said benzodiazole-tagged (co)polymer scale inhibitor.

An advantage of the reactive fluorescent compounds of this invention is that in their use in the formation of a tagged (co)polymer, the reactive fluorescent compound is not significantly affected by other structures in the (co)polymer or by other ingredients in the system.

A further advantage of the tagged (co)polymers of this invention is that the spectral properties, i.e., both excitation and emission of the (co)polymers may be in the visible wavelength region, thus allowing the use of solid state instrumentation and potentially minimize interferences that generally occur in the UV wavelength region.

EXAMPLES

Synthesis of (4-(benzo[c][1,2,5]thiadiazol-7-yl)phenyl)methanamine hydrochloride salt

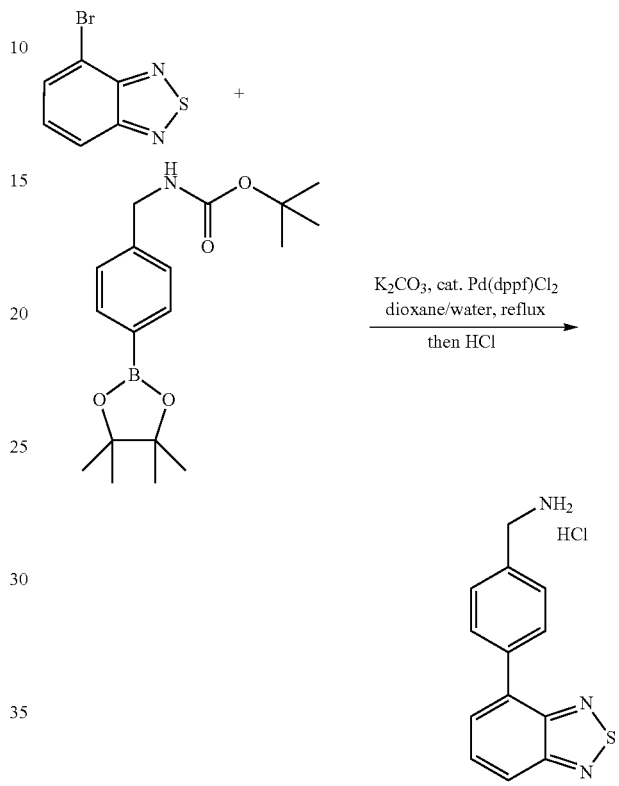

A 100 mL round bottom flask is charged with 4-bromobenzo[c][1,2,5]thiadiazole (1.61 g, 7.49 mmol, 1.00 equiv), tert-butyl (4-(4,4,5,5-tetramethyl-1,3,2-dioxaborolan-2-yl)benzyl)carbamate (2.74 g, 8.24 mmol, 1.10 equiv), potassium carbonate (3.10 g, 22.5 mmol, 3.00 equiv), and [1,1'-bis(diphenylphosphino)ferrocene]dichloropalladium (II) (0.274 g, 0.374 mmol, 5.00 mol %). The flask is connected to a reflux condenser and is placed under a nitrogen atmosphere. 38 mL of nitrogen-sparged 9:1 dioxane:water is added and the mixture was stirred at 100° C. overnight.

The solution is cooled and quenched with water. Product is extracted with several portions of dichloromethane. Combined organic fractions are dried with $MgSO_4$, concentrated, and purified by chromatography on silica gel (20% EtOAc in hexane). A white solid is isolated.

The material is immediately dissolved in 30 mL dichloromethane and 3 mL concentrated HCl are added. The mixture is stirred at ambient temperature overnight. The slurry is filtered, and the isolated white solid is rinsed with a few additional portions of dichloromethane. The solid is dried in a vacuum oven for several hours. Proton/Carbon NMR are consistent with the HCl-salt of the desired product.
$^1$H NMR (500 MHz, DMSO-$d_6$) δ 8.62 (s, 3H), 8.11 (dd, J=8.7, 1.1 Hz, 1H), 8.06-7.96 (m, 2H), 7.88 (dd, J=7.0, 1.1 Hz, 1H), 7.82 (dd, J=8.6, 7.0 Hz, 1H), 7.68 (d, J=8.1 Hz, 2H), 4.11 (s, 2H). $^{13}$C NMR (126 MHz, DMSO-d$_6$) δ 154.95, 152.61, 136.77, 134.14, 132.71, 130.08, 129.16, 129.07, 128.01, 120.61, 41.81.
Copolymer Tagging.

Example 1

A copolymer of acrylic acid, 2-acrylamido-2-methyl propane sulfonic acid, and tert-butyl acrylamide, is tagged with the (4-(benzo[c][1,2,5]thiadiazol-7-yl)phenyl)methanamine hydrochloride salt disclosed herein above using the following procedure:

A 20 mL scintillation vial is charged with 2.33 g of the copolymer (43 to 44 weight percent in water), 1.3 mL dimethylacetamide, and 2.8 mL dioxane. Then (4-(benzo[c][1,2,5]-thiadiazol-7-yl)phenyl)methanamine hydrochloride salt (0.0935 mmol, 1.00 equiv) is added, followed by 98 μL diisopropylethylamine (0.56 mmol/6.0 equiv). The mixture stirred for a few minutes until the solution is homogeneous. Then, the vial is charged with 36 mg N-(3-dimethylaminopropyl)-N'-ethylcarbodiimide hydrochloride (0.18 mmol/2.0 equiv). The mixture is stirred at ambient temperature overnight. The reaction is quenched with 3 mL of 5M aqueous NaOH to convert the polymer to the sodium salt. The solution is added to 300 mL of methanol, which precipitated the sodium salt of the copolymer. The solids are collected by filtration, and re-dissolved in about 3 mL 5M NaOH and about 2 mL water. The precipitation/filtration sequence is repeated. The final isolated solids are dissolved in about 10 mL water and the polymer is converted back to the acidic form by treatment with DOWEX™ 50 W X8 beads until the solution is acidic (pH between 2 to 4). The solids are removed by filtration, and water is removed by evaporation in a vacuum oven.

Photoluminescence data (uncorrected) is collected on aqueous solutions of Example 1 (the tagged copolymer (19 ppm)) and Comparative Example A (the untagged copolymer). Deionized water (pH 4.2) is utilized and shown in FIG. 1. The fluorescence emission spectra (uncorrected) are recorded on a Photon Technology International (PTI) fluorescence spectrophotometer at 25° C. A 75 W Xenon continuous lamp is used for data acquisition, and data analysis was performed using the FelixGX version 4.1.2.4565 software package. Fluorescence measurements are taken on aqueous samples in a 1 cm-diameter cuvette. Polymers are dissolved in deionized water with pH 4.2, unless otherwise noted.
Development of Concentration/Emission Response Curves.

25.0 mg of Example 1 is dissolved in enough deionized water (pH 4.2) to prepare 500 mL of a 50 ppm solution of the copolymer. The stock solution is diluted to prepare solutions at concentrations between 0.5 and 40 ppm. Photoluminescence data is collected for each sample using the excitation and emission values shown in Table 1.

TABLE 1

| Fluorescent Tag | Excitation Wavelength (nm) | Observed Emission Wavelength (nm) |
|---|---|---|
| Benzothiadiazole (BTD) | 315 | 500 |

Figure 2:
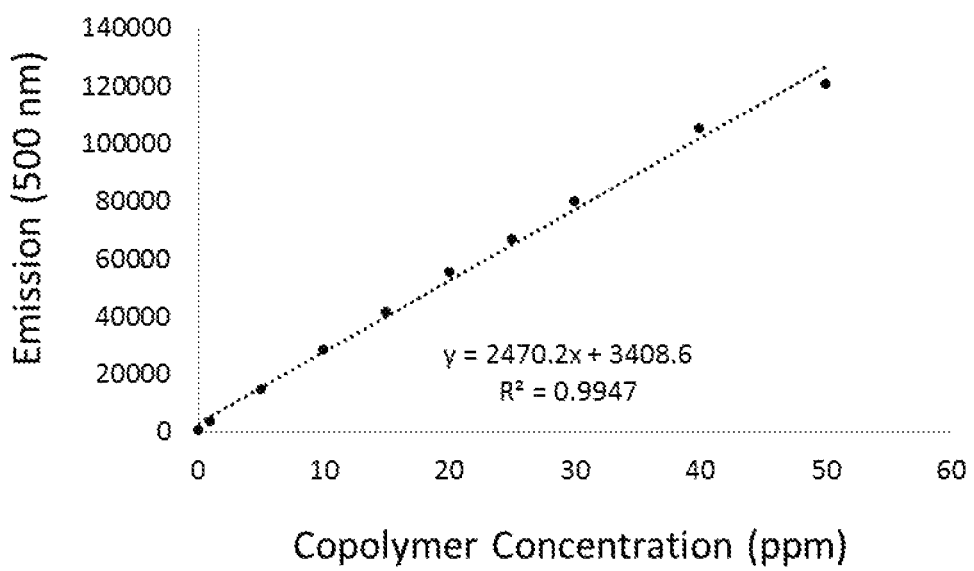
FIG. 2 is a concentration/emissions response curve for Example 1.

Plots of sample emission as a function of copolymer concentration are generated, and fit to a linear trend line and shown in FIG. 2.

Evaluation of pH influence on Emission Intensity.

Figure 3:
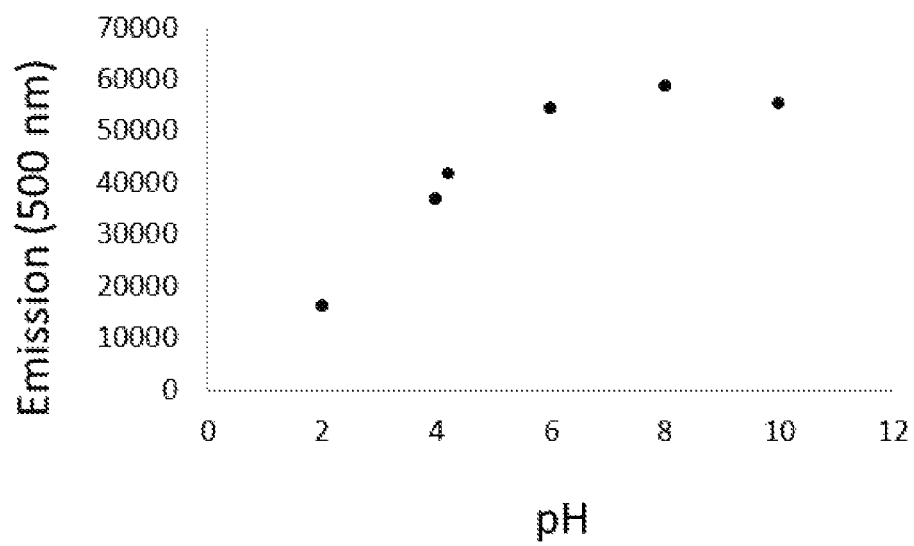
FIG. 3 is a plot of emission versus pH for Example 1.

25.0 mg of Example 1 is dissolved in enough deionized water (pH 4.2) to prepare 500 mL of a 50 ppm solution of the copolymer. The stock solution is diluted with appropriate pH buffers to prepare solutions of 15 ppm polymer. Photoluminescence data is collected for each sample using the excitation and emission values shown in Table 1. Plots of emission intensity for the 15 ppm polymer samples at each pH are prepared and observed at pH=4.2, FIG. 3.
Evaluation of NaOCl Influence on Emission Intensity.

5.0 mg of Example 1 is dissolved in enough deionized water (pH 4.2) to prepare 500 mL of a 10 ppm solution of the copolymer. A 1300 ppm solution of sodium hypochlorite (bleach) is prepared by diluting 108 mL of 6.0% bleach to 500 mL with deionized water. Three 100 mL portions of each of Example 1 copolymer solution are dispensed into bottles and are treated with portions of the sodium hypochlorite solution in varying amounts:

1) 77 μL NaOCl solution (to make solution 1 ppm NaOCl),
2) 385 μL NaOCl solution (to make solution 5 ppm NaOCl), and
3) 769 μL NaOCl solution (to make solution 10 ppm NaOCl).

The solutions are mixed well and are allowed to stand for 2 hours before photoluminescence data is collected for each sample using the excitation and emission values shown in Table 1. Data collection is also performed at 24 hours.

Figure 4:
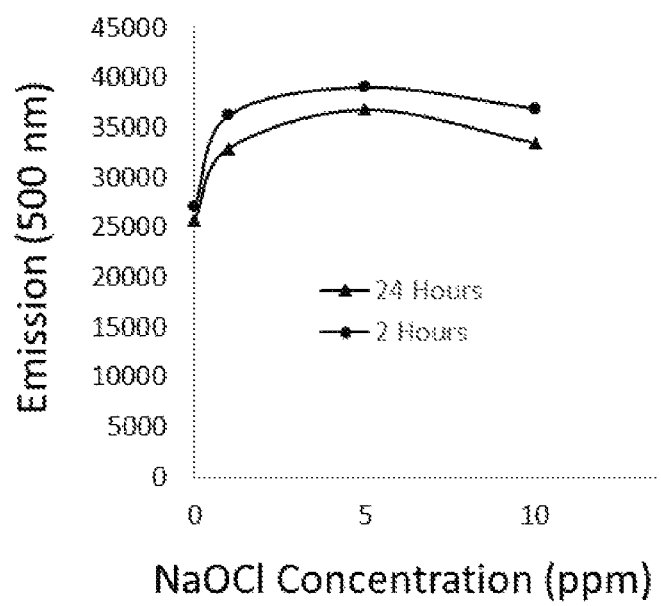
FIG. 4 shows the effect of NaOCl concentration on the fluorescence of Example 1.

Using the data points from both times, a plot of emission intensity a
s a function of NaOCl concentration is generated and shown in FIG. 4.

Evaluation of Scale Inhibition Performance.

Figure 5:
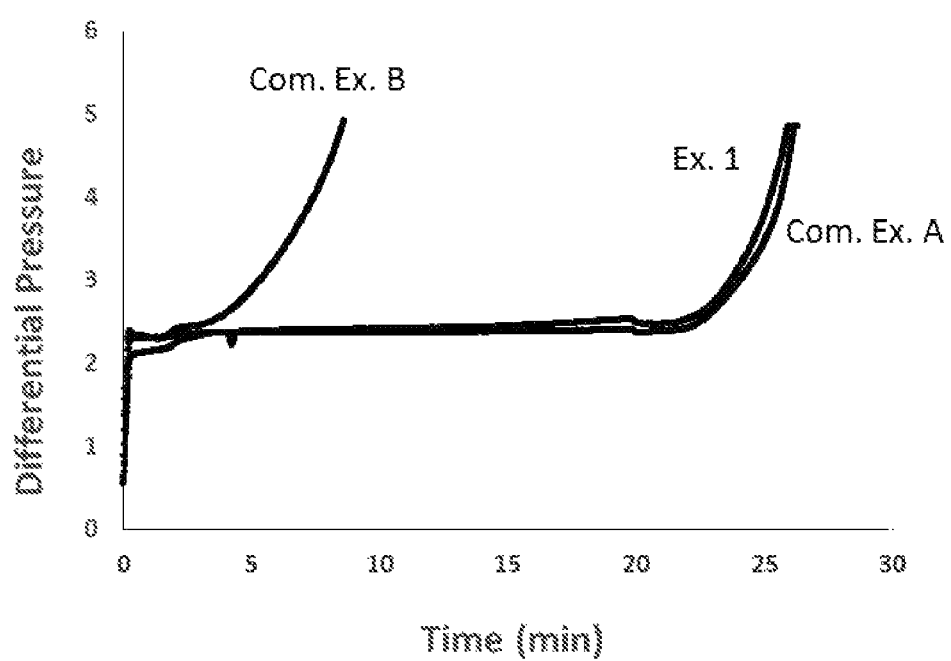
FIG. 5 is a plot of scale inhibition for Example 1 and Comparative Example A.

The performance of Example 1, Comparative Example A, and Comparative Example B (blank—no scale inhibitor) are evaluated against calcium carbonate scale using dynamic tube block testing with a DSL instrument (PSL Systemtechnik Germany). A calcium-containing brine (12.15 gCaCl$_2$*2H$_2$O/L, 3.680 g MgCl$_2$*6H$_2$O/L, 33 g NaCl/L) and a bicarbonate-containing brine (7.36 g NaHCO$_3$/L, 33 g NaCl/L) are combined at 71° C. (covered by NACE TM0374 Method) and the differential pressure is measured over a piece of 1/16 inch diameter stainless steel tubing over time as the inhibitor concentration is decreased by 5 ppm every 20 minutes starting at 25 ppm. The minimum inhibitor concentration (MIC) refers to the minimum concentration of scale inhibitor at which the stainless steel tube does not block. The results are shown in FIG. 5.

The MIC for Example 1 and Comparative Example A are shown in Table 2.

TABLE 2

|  | MIC (ppm) |
|---|---|
| Comparative Example A | 20 |
| Example 1 | 20 |

What is claimed is:
1. A method for maintaining a desired amount of benzodiazole-tagged (co)polymer in an industrial water system comprising the steps of:
   a) adding a benzodiazole-tagged (co)polymer to water such that a desired concentration of said benzodiazole-tagged (co)polymer is present in said water, wherein the benzodiazole-tagged (co)polymer comprises:

(i) a benzodiazole compound, or salt thereof, represented by one of the following formulas:

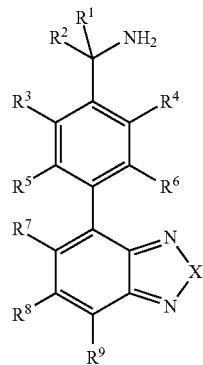
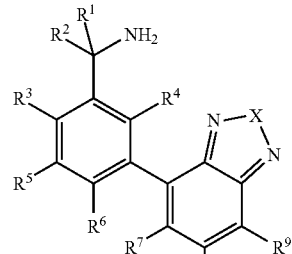
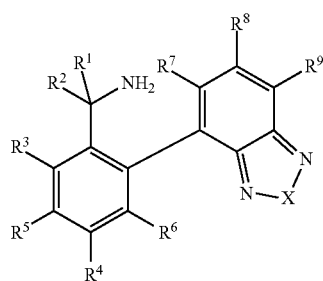
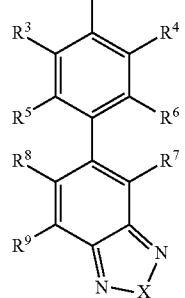
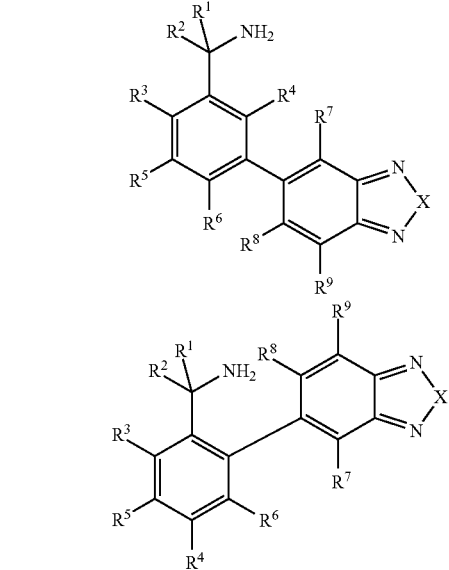

wherein $R^1$ to $R^9$ are independently H, a $C_1$ to $C_{12}$ alkyl group, a $C_1$ to $C_{12}$ aryl group, $-SO_3^-$, $-PO_3^{2-}$, $-CO_2^-$, or $-N^+R^{10}_3$, wherein each $R^{10}$ is independently H or $C_1$ to $C_{12}$ alkyl and X is oxygen or sulfur, b) using a fluorometer to detect a fluorescent signal of said benzodiazole-tagged (co)polymer;

c) converting the fluorescent signal of the (co)polymer to a concentration of said benzodiazole-tagged (co)polymer; and d) adjusting the concentration of said benzodiazole-tagged (co)polymer according to what the desired concentration is for said benzodiazole-tagged (co)polymer in the industrial water system.

2. The method of claim 1 wherein the benzodiazole compound, or salt thereof, (i) has the formula:

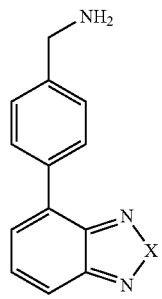

wherein X is oxygen or sulfur.

3. The method of claim 1 wherein the benzodiazole-tagged (co)polymer comprises:
(ii) at least one monoethylenically unsaturated acid monomer and
(iii) optionally, at least one monoethylenically unsaturated acid-free monomer.

4. The method of claim 3 wherein
(ii) the monoethylenically unsaturated acid monomer is selected from acrylic acid, methacrylic acid, crotonic acid, vinylacetic acid, maleic acid, maleic anhydride, 1,2,3,6-tetrahydrophthalic anhydride, 3,6-epoxy-1,2,3, 6-tetrahydrophthalic anhydride, 5-norbornene-2,3-dicarboxylic anhydride, bicyclo-[2.2.2]-5-octene-2,3-dicarboxylic anhydride, 3-methyl-1,2,6-tetrahydrophthalic anhydride, 2-methyl-1,3,6-tetrahydrophthalic anhydride, itaconic acid, mesaconic acid, fumaric acid, citraconic acid, 2-acrylamido-2-methylpropanesulfonic acid, allylsulfonic acid, allylphosphonic acid, allyloxybenzenesulfonic acid, 2-hydroxy-3-(2-propenyloxy)-propanesulfonic acid, isopropenylphosphonic acid, isopro-penylsulfonic acid, vinylphosphonic acid, styrenesulfonic acid, vinylsulfonic acid, and the alkali metal or ammonium salts thereof and
(iii) if present, the monoethylenically unsaturated acid-free monomer is selected from methyl acrylate, ethyl acrylate, butyl acrylate, methyl methacrylate, ethyl methacrylate, butyl methacrylate and isobutyl methacrylate; hydroxyalkyl esters of acrylic or methacrylic acids such as hydroxyethyl acrylate, hydroxypropyl acrylate, hydroxyethyl methacrylate, hydroxypropyl methacrylate, acrylamide, methacrylamide, N-t-butylacrylamide, N-methylacrylamide, N,N-dimethyl-acrylamide, acrylonitrile, methacrylonitrile, allyl alcohol, phosphoethyl methacrylate, 2-vinylpyridene, 4-vinylpyridene, N-vinyl-pyrrolidone, N-vinylformamide, N-vinylimidazole, vinyl acetate, and styrene.

5. The method of claim 3 wherein
(ii) the monoethylenically unsaturated acid monomer is selected from acrylic acid, methacrylic acid, 2-acrylamido-2-methylpropanesulfonic acid, or maleic acid, and
(iii) if present, the monoethylenically unsaturated acid-free monomer is selected from methyl acrylate, ethyl acrylate, butyl acrylate, methyl methacrylate, ethyl methacrylate, acrylamide, methacrylamide, N-t-butylacrylamide, N-methylacrylamide, or N,N-dimethylacrylamide.

6. A method to inhibit scale in an industrial water system comprising the steps of:
   a) providing a scale inhibitor for an industrial water system susceptible to unwanted scaling and
   b) adding to the water of said industrial water system from 0.1 ppm to 50 ppm of a scale inhibitor;
   wherein said scale inhibitor is a benzodiazole-tagged (co)polymer comprising:
   (i) a benzodiazole compound, or salt thereof, represented by one of the following formulas:

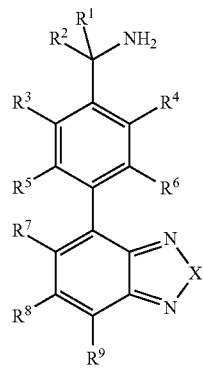
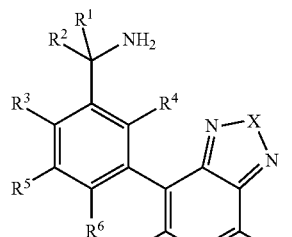
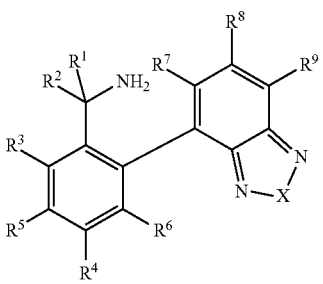
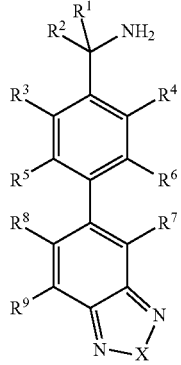
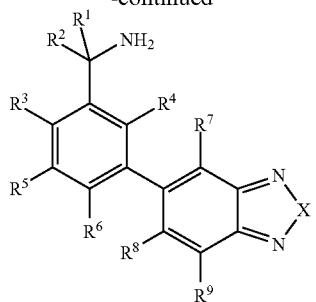
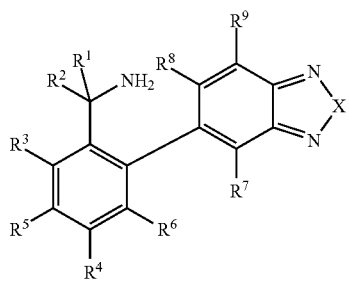

wherein $R^1$ to $R^9$ are independently H, a $C_1$ to $C_{12}$ alkyl group, a $C_1$ to $C_{12}$ aryl group, $-SO_3^-$, $-PO_3^{2-}$, $-CO_2^-$, or $-N^+R^{10}{}_3$ wherein each $R^{10}$ is independently H or $C_1$ to $C_{12}$ alkyl and X is oxygen or sulfur.

* * * * *